United States Patent [19]

Pourprix

[11] Patent Number: 5,621,208
[45] Date of Patent: Apr. 15, 1997

[54] PARTICLE, PARTICULARLY SUBMICRON PARTICLE SPECTROMETER

[75] Inventor: Michel Pourprix, Nontlhéry, France

[73] Assignee: Commissariat a l'Energie Atomique, Paris, France

[21] Appl. No.: 439,768

[22] Filed: May 12, 1995

[30] Foreign Application Priority Data

May 24, 1994 [FR] France .................................. 94 06274

[51] Int. Cl.$^6$ .................................................. H01J 49/40
[52] U.S. Cl. ........................................... 250/287; 250/281
[58] Field of Search ................................... 250/287, 288, 250/289, 283, 282, 281; 324/464, 452, 457

[56] References Cited

U.S. PATENT DOCUMENTS

| | | | |
|---|---|---|---|
| 4,556,849 | 12/1985 | Kalakutsky et al. | 324/464 |
| 5,047,723 | 9/1991 | Puumalainen | 250/287 |
| 5,117,190 | 5/1992 | Pourprix . | |
| 5,455,417 | 10/1995 | Sacristan | 250/287 |

FOREIGN PATENT DOCUMENTS 0404681  12/1990  European Pat. Off. .

OTHER PUBLICATIONS

Transactions of the IEEE on Nuclear Science, vol. NS–19, No. 1, Feb. 1, 1972, pp. 64–74, Raabe, "Instruments And Methods For Characterizing Radioactive Aerosols' Electrostatic Samplers". pp. 66–67.

Aerosol Science and Technology, vol. 13, Oct. 1, 1990, pp. 230–240, Wang et al., "Scanning Electrical Mobility Spectrometer"., p. 232 –p. 235.

Journal of Aerosol Science, vol. 6, Dec. 1, 1975, pp. 443–451, Knutson et al., "Aerosol Classification By Electric Mobility, Etc.".

Review of Scientific Instruments, vol. 51, No. 8, Aug. 1, 1980, pp. 1098–1104, Schowengerth et al., "A Parallel Plate Electrostatic Size Classifier, Etc.".

Primary Examiner—Jack I. Berman
Assistant Examiner—Kiet T. Nguyen
Attorney, Agent, or Firm—Pearne, Gordon, McCoy & Granger

[57] ABSTRACT

An electrical mobility spectrometer for aerosol particles of an atmosphere to be examined comprises a first (18) and a second (20), spaced, parallel, coaxial conductive disks between which is established an electric field, an annular slot (22) formed in the first disk for communicating with the atmosphere to be examined, a central intake (26) for bringing about a circulation from the periphery of the disks of a centripetal, stable, laminar filtered air flow, an annular slot (28) made in the second disk, a device for varying the selected electrical mobility and an aerosol detector or collector (17).

17 Claims, 9 Drawing Sheets

PARTICLE, PARTICULARLY SUBMICRON PARTICLE SPECTROMETER

TECHNICAL FIELD

The present invention relates to a novel particle spectrometer more particularly making it possible to determine the grain size distribution of aerosol particles suspended in air or another gas covering a size range between 1 nanometer ($10^{-9}$ m) and a few micrometers ($10^{-6}$ m).

Among other applications, said spectrometer is e.g. particularly suitable for determining the grain size spectrum of the atmosphere aerosol for the continuous monitoring of the air quality in installations or in the environment.

PRIOR ART

At present one of the highest performance means for determining the grain size distribution of submicron aerosols consists of measuring the electronic mobility spectrum of the particles, whereof the charge law is known. For the better understanding of the remainder of the present text, it is pointed out that in stationary equilibrium in a given volume of atmosphere, the total sum of the positive and negative electric charges carried by the particles of an aerosol located therein is zero. This means that at all times, the sample contained in said atmosphere part has the same number of positive charges as negative charges, generally in accordance with a Gauss distribution centered on the zero charge and decreasing as a function of the number of elementary charges and this is the so-called Boltzmann's law.

Consequently, frequent use has already been made for the selection of aerosols, of electrostatic fields acting on the electrical charges which they carry. To this end, definition takes place of a fundamental notion in this field, which is the electrical mobility of a charged particle placed in an electrostatic field. This quantity, which defines the varying aptitude of such a particle to undergo a deviation under the effect of this field can be represented by the following vector equation:

$$\vec{W} = Z\vec{E},$$

in which $\vec{W}$ is the drift velocity acquired by the particle under the influence of the electrical field E to which it has been exposed. The proportionality coefficient Z between the two aforementioned quantities is the electrical mobility in question. As is also in accordance with intuition, this electrical mobility is on the one hand proportional to the electrical charge of the particle and on the other inversely proportional to its grain size, there is a possibility of producing true electrical mobility spectrometers consisting of subjecting aerosol particles entrained in a gaseous flow to the action of an electric field present between two electrodes. Under the effect of the field, the charged particles of said aerosols will be deposited, as a function of their sign, on one of the said electrodes and the abscissa of their deposition with respect to the direction of the gaseous flow is characteristic of their mobility in the sense that the higher said electrical mobility, the lower the abscissa of their deposit. Thus, there is a spread in space of the collected particles, performing spectrometry thereof as a function of their electrical mobility.

An apparatus based on this principle is described in French certificate of addition 90 02413 of 27.2.1990, published under No. 2 658 916 (U.S. Pat. No. 5,117,190) entitled "Electrostatic aerosol particle sensor and apparatuses incorporating the application thereof". This type of apparatus is illustrated in FIG. 1 and has two spaced, parallel, coaxial conductive disks 2, 4 between which is established a potential difference V and therefore a uniform electric field $\vec{E}$. The disk 2 has an annular slot 6 (radius $r_1$) by which are introduced the particles to be analyzed at a flow rate $q_1$. A central intake 8 is provided by which an air flow Q circulates under the effect of a not shown pump.

The charged particles having the requisite electrical mobility are entrained to a second annular slot 10 of radius $r_2$ made in the disk 4 under the combined action of a filtered air flow at the rate $q_0$, which is radial and laminar and established between the two disks and the electrical field E imposed between the two disks.

Through the slot 10 the air flows at a rate $q_2$ into a cylindrical box 12 attached beneath the disk 4, which gives $Q = q_0 + q_1 - q_2$. The particles which traverse the slot 10 have the same electrical mobility $Z = Q/\pi E(r_1^2 - r_2^2)$.

In order to regulate this electrical mobility to the desired value in each individual case, it is possible to act on two parameters namely the flow rate Q on the one hand and the potential difference V applied between the two coaxial, conductive disks 2 and 4 on the other.

By means of the cylindrical box 12 and a pipe 14, the particles can then be directed to a detector.

Although satisfactory in certain respects, this type of apparatus still suffers from certain shortcomings and in particular if it is used for selecting nanometric size particles.

Firstly, the transport of particles having a nanometric size in circuits of the system leads to losses by Brown scattering in the vicinity of the walls, particularly in the cylindrical box 12, the discharge pipe to the detector and in the actual detector. For information purposes, a 30 cm long pipe at a flow rate of 0.3 l/min collects by Brown scattering approximately 50% of the 3 nanometer particles.

Secondly, as a result of the laminar flow conditions in the circuits, the particles in the center of the pipes move faster than those in the vicinity of the walls and consequently there is a spread of the transit time of the particles through the apparatus, which is prejudicial to the accuracy of counting by the detector, particularly when the electrical field is a function of time.

DESCRIPTION OF THE INVENTION

The object of the invention is to solve these problems.

The invention therefore relates to an electrical mobility spectrometer for aerosol particles contained in an atmosphere to be examined, comprising a first and a second, spaced, parallel, coaxial conductive disks between which is established an electric field by raising them to different potentials, the space between the two disks communicating with the atmosphere to be examined through an annular slot of radius $r_1$ made in the first disk, a central intake being provided in order to bring about the circulation in said space, from the periphery of the disks, of a stable, centripetal, laminar filtered air flow, and the second disk is provided with an annular opening of radius $r_2$ ($r_2 < r_1$) so as to permit the selection of aerosol particles having a given electrical mobility, characterized in that it also comprises means able to vary the selected electrical mobility and an aerosol detector.

In an apparatus of the type according to the invention, the spectrometer also has an aerosol collector associated with said detector.

The invention makes it possible to obviate the need for the cylindrical box 12 (FIG. 1), so that losses therein are avoided. It is also more compact due to the absence of the box 12.

According to an embodiment, the annular opening is reduced to a single central extraction orifice.

This configuration makes it possible to extract the particles precisely in the axis of the apparatus. Therefore the particles travel in a laminar flow without contact with the walls (and therefore without losses), with identical transit times and following identical trajectories. The transit times are also easy to determine, because the geometrical dimensions of the system can be easily determined.

If the spectrometer has a collector, the latter can be of the mechanical or electrostatic type.

A mechanical collector can be associated with a detector, particularly of the electrometer type. In this case, it is possible to produce a submicron aerosol grain size spectrometer.

An electrostatic collector can be associated with a nuclear detector for the analysis of radioactive aerosols. In this case, it is possible to produce a submicron particle grain size spectrometer incorporating such an electrical mobility spectrometer, associated with means for the processing of the signal obtained by the detector and which can be so programmed that, from an electrical mobility spectrum obtained at the detector outlet, can be obtained an aerosol grain size spectrum.

According to another aspect, the electrostatic collector can incorporate:

a third conductive disk facing the second disk and forming a collection surface for selected particles, means for injecting into the space between the second and third disks, a radial, laminar, filtered air flow from the periphery of said two latter disks, a central pipe fixed to the second disk and permitting the suction of the atmosphere between the second and third disks.

According to another embodiment, a spectrometer according to the invention can also incorporate:

a third conductive disk facing the second disk, means for injecting into the space between the second and third disks, a radial, laminar, filtered air flow from the periphery of said two latter disks, a central pipe fixed to the third disk by which the particles are fed into a detector in order to count them.

In said latter configuration, a second stage is formed with the aid of the third and second disks and a "dynamic confinement" is obtained with the aid of a filtered air flow between said two disks. This flow channels the particles as from their extraction from the first stage constituted by the first and second disks. Then passing out of the second stage, the particles are passed into a pipe ensuring their transfer to the outside, still in laminar flow, with the special feature that they are confined in the vicinity of the center of the flow without contact with the walls (therefore without loss) and with identical trajectories (therefore with identical transit times).

Moreover, said apparatus is more particularly suitable for an optimum coupling with several types of detectors, which makes it possible to envisage:

a high analyzer/detector integration within the same, very compact assembly, an excellent sensitivity, even for nanometric sizes, because the particles are carried without losses on the walls, a precision with respect to the results unattainable with any prior art apparatus, said precision being linked with the perfect control of the particle transmit times in the different compartments of the system.

The detector can be chosen from among the following apparatuses:

an optical particle counter of the "condensation nucleus counter type" able to detect particles as fine as atmospheric ions (~1 nm) for fixed supersaturation conditions, an electrometer of the charge integration type (for high concentrations) or the pulse type (for low concentrations), a nuclear detector for radioactive aerosols.

Here again, the apparatus can be combined with means for processing signals from the detector, in order to obtain a particle grain size spectrometer.

BRIEF DESCRIPTION OF THE DRAWINGS

The features and advantages of the invention can be better gathered from the following description of non-limitative embodiments and with reference to the attached drawings, wherein show.

DETAILED DESCRIPTION OF THE EMBODIMENTS

Figure 1:
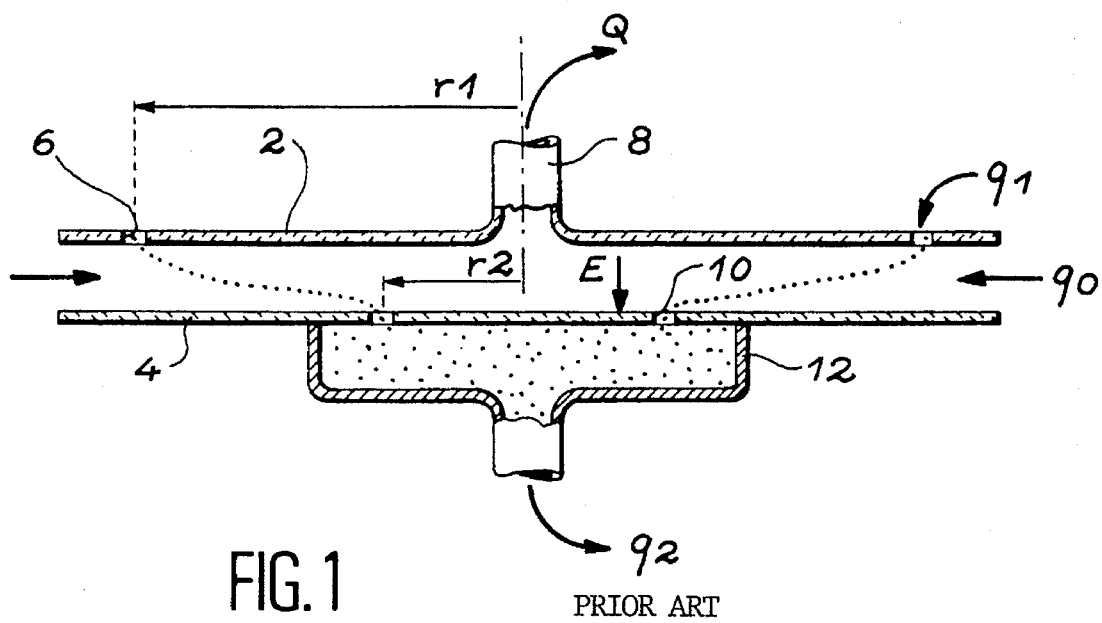
FIG. 1 An electrostatic aerosol particle spectrometer according to the prior art.
Figure 2A:
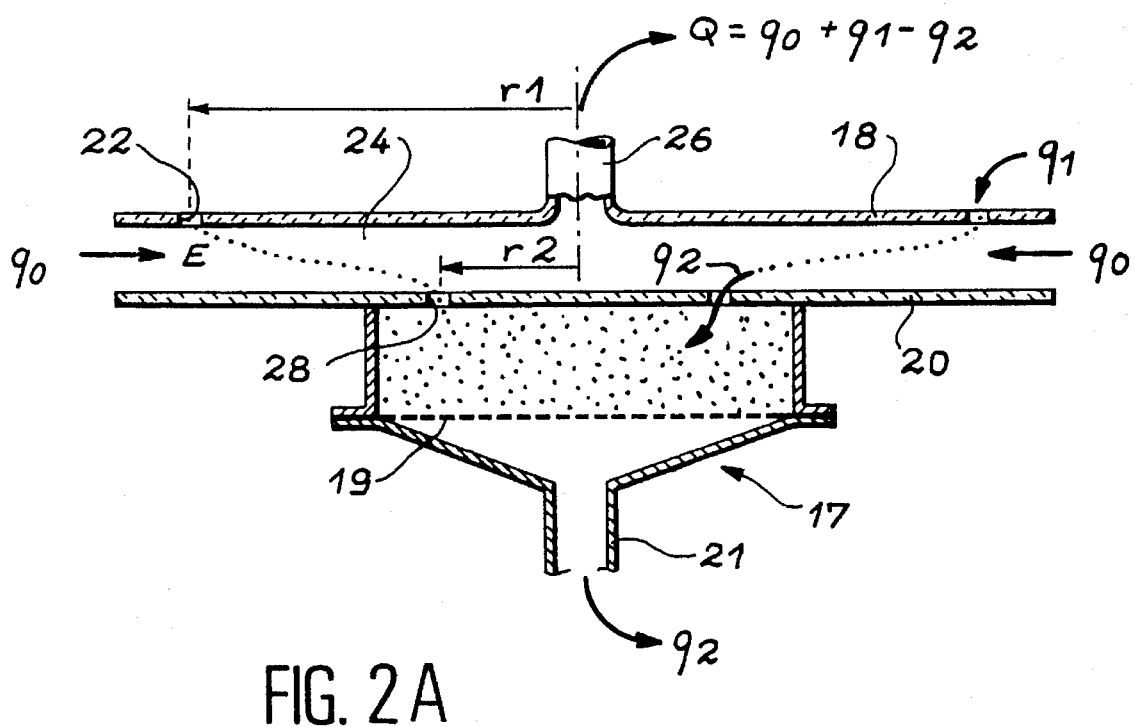
FIGS. 2A and 2B A particle spectrometer according to the invention.

FIG. 2A is a diagram of an apparatus according to the invention. This apparatus firstly comprises a circular electrical mobility selector (GEMS) having two concentric disks 18, 20. The first disk 18 has an annular slot 22 of radius $r_1$ by means of which a gas sample containing the particles to be analyzed is introduced at a flow rate $q_1$. A central suction tube or pipe 26 makes it possible to extract an air flow Q from the space between the two disks. As the two disks are conductive, each of them can be raised to a certain potential and an electric field $\vec{E}$ can be established in the space 24 separating them. In the second disk 20 is formed an annular opening 28 of radius $r_2$, which will be traversed by an air flow $q_2$. Between the two disks and on the periphery of the space 24 is injected at the rate $q_0$ and using means not shown in FIG. 2A, an entrainment gas (filtered air), so that a laminar flow circulates between the two disks up to the central suction tube 26, which consequently absorbs a flow rate $Q=q_0+q_1-q_2$.

If Z is the electrical mobility of the particles, 2 h the distance separating the disks 18 and 20, V the potential difference between these disks, the theory of the apparatus shows that the aerosol particles traversing the slot of radius $r_2$ have a mobility Z such that:

$$r_2 = \sqrt{r_1^2 - \frac{2Qh}{\pi ZV}}$$

The spectrometer according to the invention also has means, which are not shown in FIG. 2A, making it possible to vary the chosen mobility Z, e.g. means for varying the flow rate Q or the voltage V in accordance with a function Q(t) or V(t). These means will be included in all the other embodiments described hereinafter.

A mechanical collector 17 collects the particles having the chosen electrical mobility Z. These particles are e.g. collected on a porous membrane 19 (very high efficiency filter) with a view to a subsequent analysis. Such an analysis can e.g. be a weighing operation or a chemical analysis.

Figure 2B:
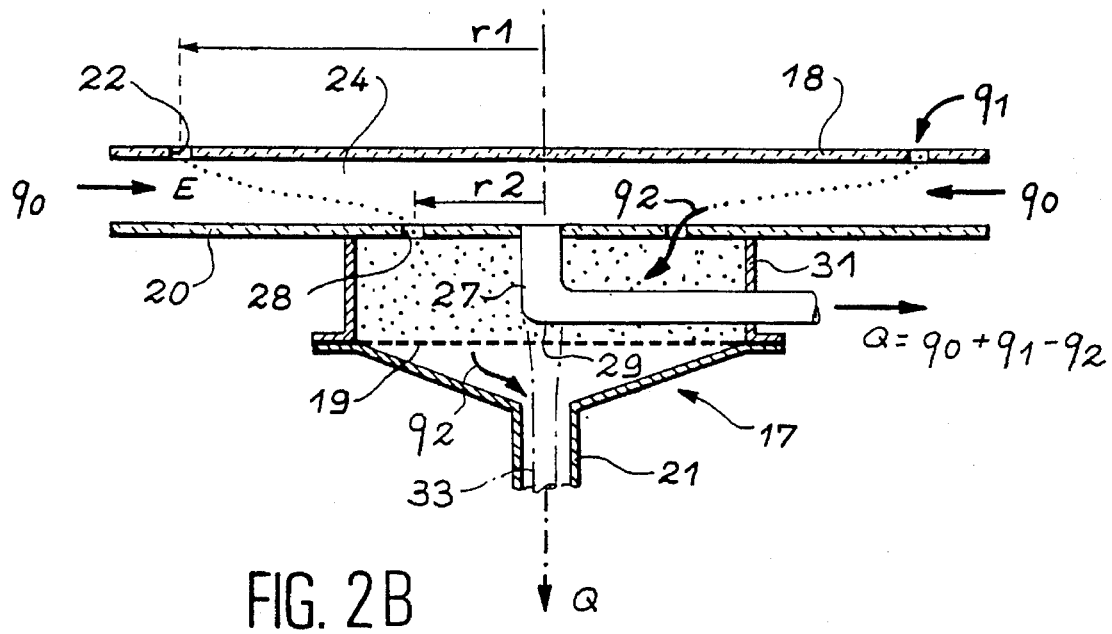

As is illustrated in FIG. 2B, a central suction tube 27 connected to the second disk 20 can be provided in place of the tube 26 connected to the first disk 18. The tube 27 has a bend 29 enabling it to pass to the side towards the outside of the box 31. It can also pass out through the lower part, in the manner shown by the broken lines 33 in FIG. 2B. This arrangement leads to a space gain on the side of the upper disk 18.

Figure 3:
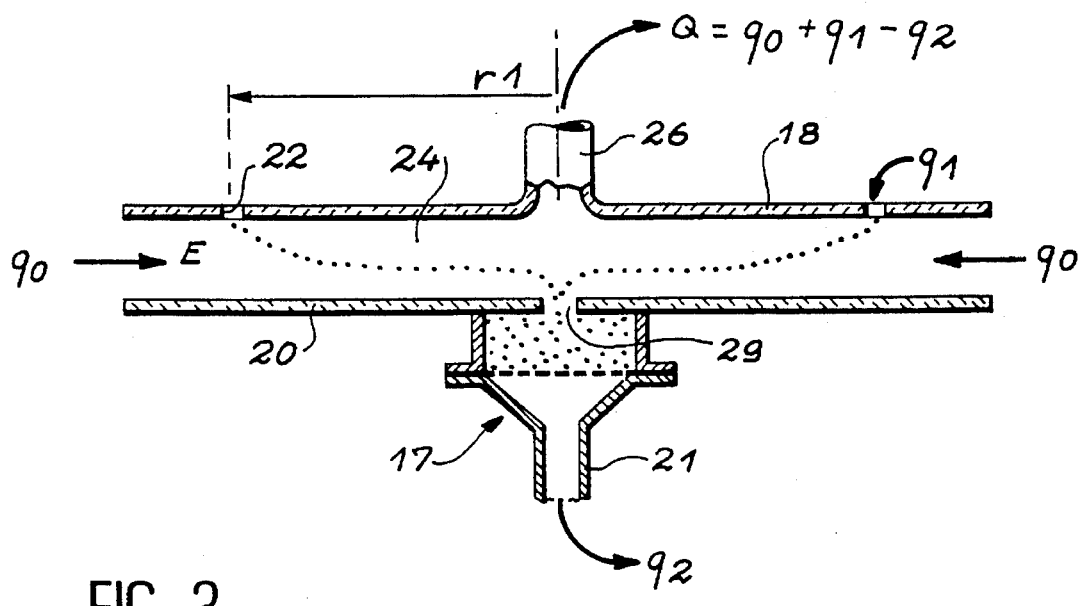
FIG. 3 A variant of the particle spectrometer according to the invention.

A variant of this embodiment is illustrated in FIG. 3, where identical components to those of FIGS. 2A and 2B are given the same references, but where the slot 28 is replaced by a single central orifice 29.

The particles arriving in the center of the second disk 20 and which are sucked at a flow rate $q_2$ through the orifice 29 have as their mobility $Z = Q/\pi E r_1^2$.

The diameter φ of the orifice 29 is preferably chosen so as to ensure a good selectivity of the particles (if the diameter is large the selectivity is low), but also in such a way as not to disturb the flow of fluid through them (if the diameter is small, a "jet" phenomenon occurs at said orifice and there can be an excessive pressure drop here).

Figure 4:
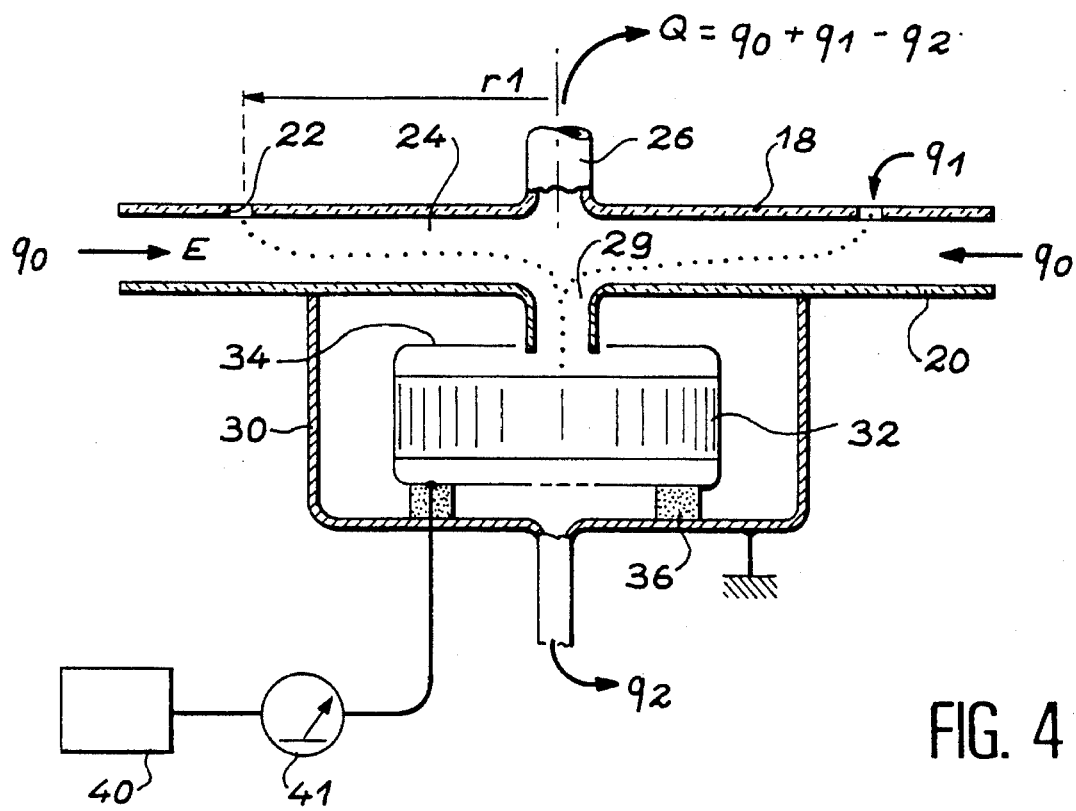
FIG. 4 A spectrometer according to the invention having an electrometer as the detector.

The spectrometer according to the invention with the annular slot which may or may not be reduced to a central extraction orifice, can also function with an electrometer as the detector. The case of a central extraction orifice is shown in FIG. 4, where the same references designate the same components as in FIG. 3. The particles are injected by the annular slot 22 and are selected as hereinbefore. The detector is essentially constituted by a Faraday cage 30, a filter 32 supported by a conductive filter holder 34 and connected by an insulating collar 36 to the cage 30. Reference 40 designates an electrometer connected to the filter holder 34. The charged particles trapped on the filter 32 induce a current i, which is measured by the electrometer 40 and the date can be collected by processing, storage and analysis means 41.

If N is the concentration of the particles to be analyzed, p the mean or average charge number carried by each particle, q the sampling flow rate through the filter, there is an electric current i such that:

$$i = qNpe$$

in which e is the elementary electronic charge.

In practice, the main applications of this method are in the case where |p|=1 (a single electric charge carried by the particles) and in this case the concentration of the particles is directly expressed by $$N = i/qe.$$

This embodiment also makes it possible to produce an aerosol grain size spectrometer. The mobility spectrum of the particles is firstly established by performing a scan of the mobility of the particles with the aid of the means provided for this purpose, e.g. a scan E=f(t) and then, on the basis of the following data:

charge law of the initial particles as a function of their size, value of the different flow rates, dimensional characteristics of the device, function E=f(t) (for the case of a voltage scan), particle transit time, impulsing rate as a function of time, it is possible to automatically return to the grain size spectrum of the initial particles by means of a computing program operating on a microcomputer especially programmed for this purpose. This program is based on a computing method like that described in the article by SL. C. Wang et al entitled "Scanning electrical mobility spectrometer", published in Aerosol Science and Technology, vol. 13, pp 230–240, 1990.

Figure 5:
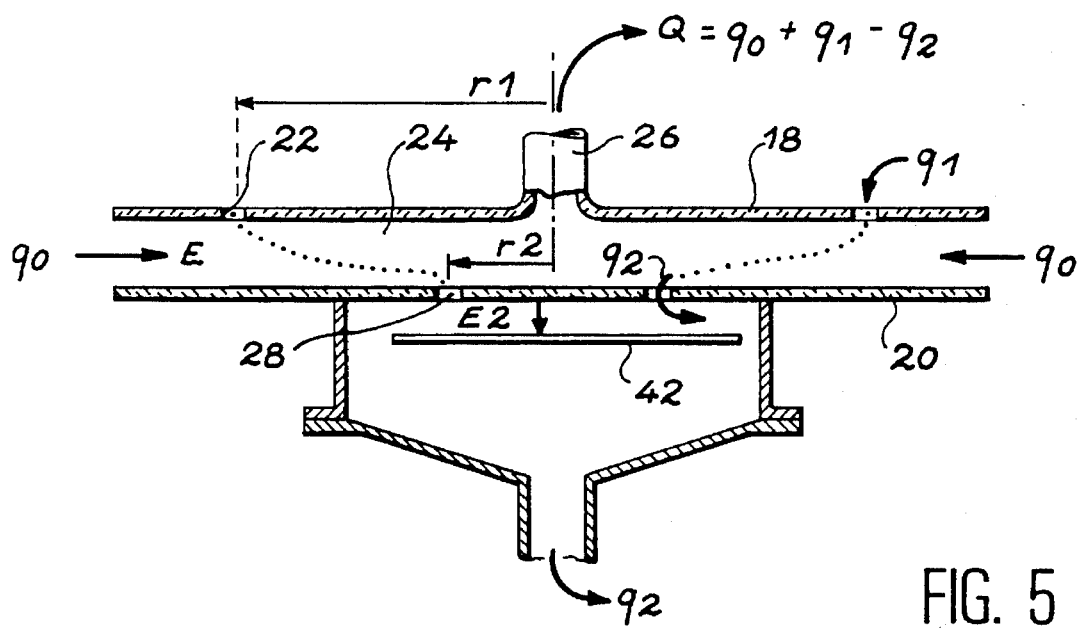
FIG. 5 A spectrometer according to the invention having an electrostatic collector.

Another variant of a spectrometer according to the invention is shown in FIG. 5, where once again the annular extraction slot 28 is advantageously reduced to a central extraction orifice as in FIG. 3. FIG. 5 uses the same references for the same components as in FIGS. 2A and 2B. In this embodiment, after selection as a function of their electrical mobility, the charged particles are deposited on an electrostatic collector, which is essentially constituted by a collection disk 42. Means which are not shown in the drawing are provided for establishing between the disk 42 and the second disk 20, a component of the selector, an electric field $E_2$, which is generally very high compared with the field E produced in the selector. The field $E_2$ makes it possible to precipitate the charged particles on the disk 42. Following the deposition of the particles, the collection disk can be used for a subsequent overall analysis.

Figure 6:
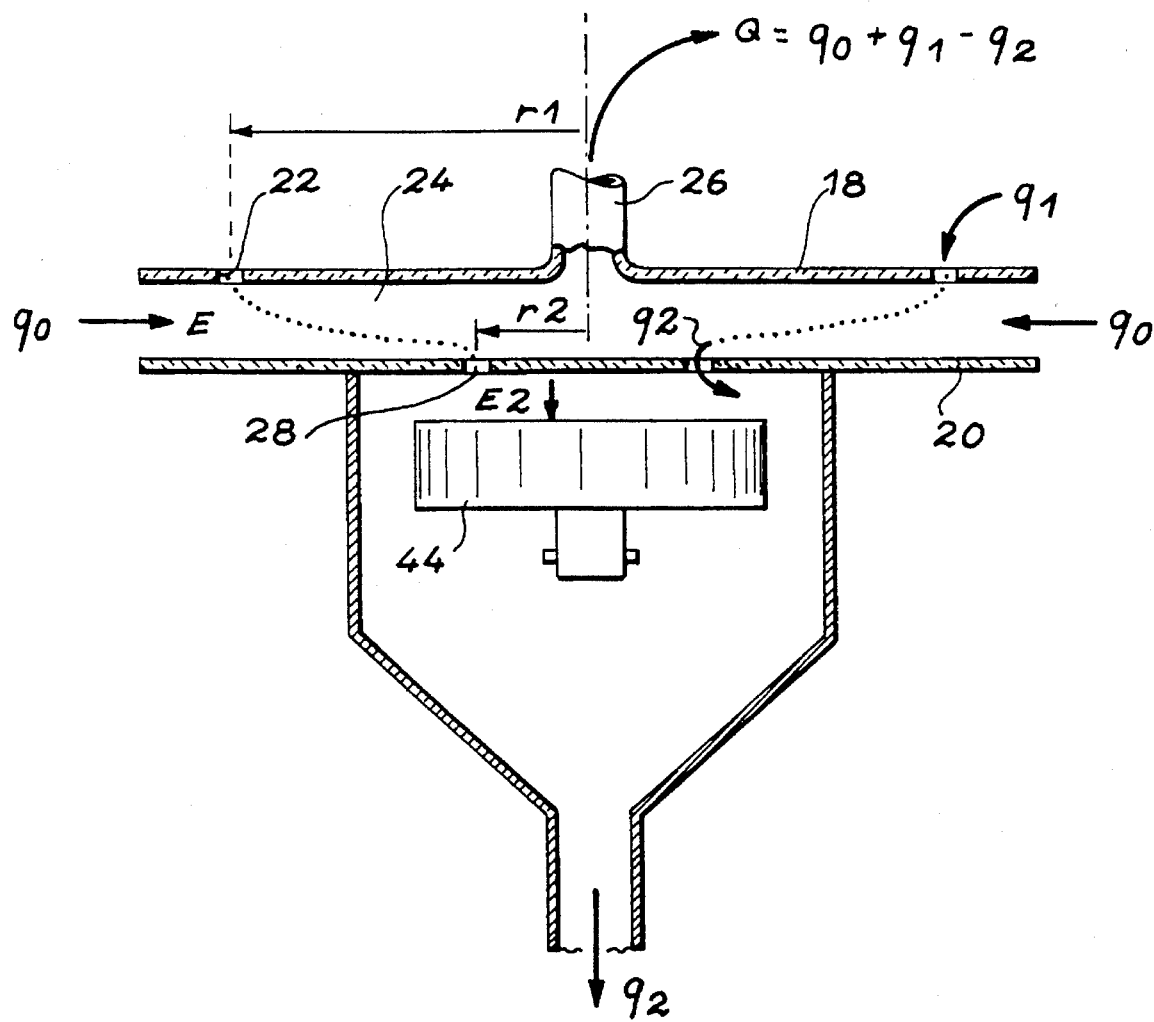
FIG. 6 A spectrometer according to the invention having a nuclear detector.

In accordance with what is illustrated in FIG. 6, the embodiment of FIG. 5 can be modified by replacing the collection disk by a detector 44, e.g. a nuclear detector for analyzing radioactive aerosols. In particular, said detector can be a surface-barrier, silicon detector with a view to a continuous analysis, e.g. for measuring the grain size of "oc emitter" radioactive aerosols, like radon daughters. Here again, means are provided for establishing between the upper surface of the detector and the second disk 20 of the selector an electric field $E_2$ making it possible to precipitate the charged particles selected by the annular slot or the central extraction orifice.

With this apparatus, it is possible to produce a grain size spectrometer. For this purpose, the selection apparatus like that illustrated by FIG. 6 is connected to means for processing the signal measured with the aid of the detector 44. As has already been stated hereinbefore, a particle mobility spectrum is firstly established with the aid of the means provided for this purpose. This is followed by a deconvolution processing of the data, functioning on a microcomputer especially programmed for this purpose, so that selected radioactive particles can be brought to the grain size. This processing must take account not only of the aforementioned data in the case of the embodiment using an electrometer, but also the effect of decreasing the activity of the radionuclides deposited on the detector, as a function of time, bearing in mind their half-life. Such an effect, for radionuclides deposited on a filter, is described in the article by R. D. Evans entitled "Engineer's guide to the elementary behaviour of radon daughters" published in Health Physics", volume 17, pp 229 to 252, 1969.

Another embodiment of the invention will now be described in conjunction with FIGS. 7A and 7B.

Figure 7A:
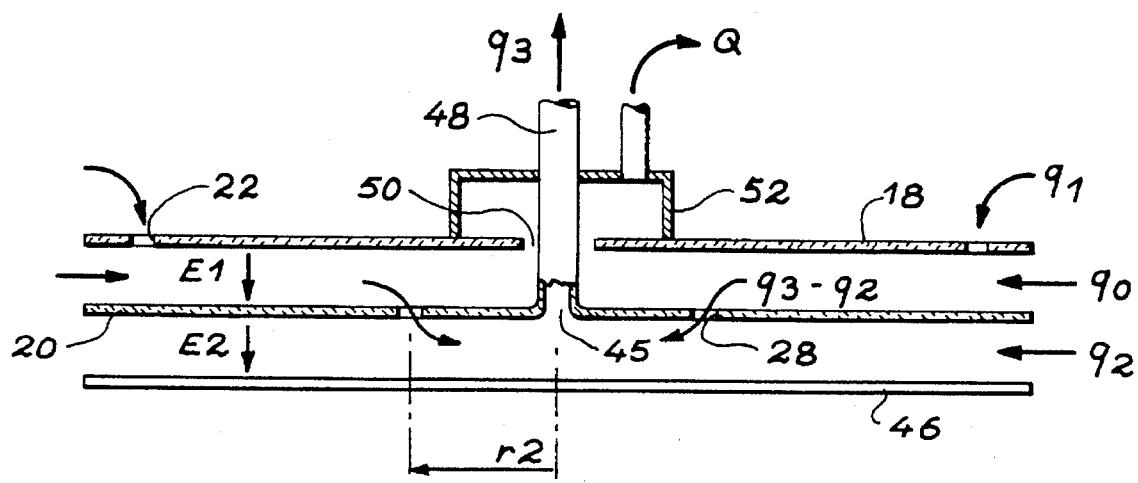
FIGS. 7A and 7B A spectrometer having an electrostatic collector and (FIG. 7B) a nuclear detector.
Figure 7B:
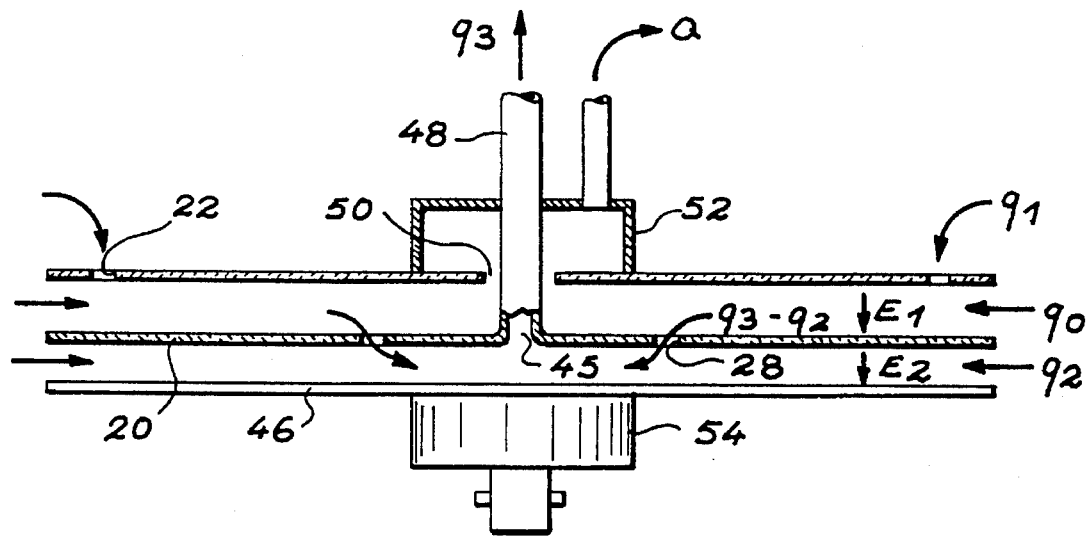

The apparatus of FIG. 7A has two concentric disk 18, 20, the first having an annular slot 22 of radius $r_1$ by means of which a gas sample containing the particles to be analyzed is introduced at a flow rate $q_1$. The two disks are conductive and means are provided for raising each of them to a certain potential and for establishing in the space separating them an electric field $E_1$. From the periphery of the two disks 18, 20 is injected, by means not shown in FIG. 7A, an entrainment gas (filtered air) at the flow rate $q_0$, in such a way that a laminar flow flows between the two disks 18, 20 up to a central opening 50 made in the first disk 18. By means of an assembly 52 constituted by a box and a suction tube, this opening makes it possible to absorb a flow rate Q. Moreover, facing the second disk 20 is provided a conductive surface 46 for collecting particles selected through the annular slot 28. Means are provided for raising the surface 46 and the disk 20 to a certain potential so as to establish, in the space between the two components, a field $E_2$ making it possible to precipitate particles on the surface 46. Means are also provided for injecting, from the periphery of the apparatus, into the space between the disk 20 and the surface 46, a radial, laminar, filtered air flow $q_2$. A suction tube 48 connected to an opening 45 made in the center of the second disk 20 permits the suction of the atmosphere between said disk 20 and the surface 46 at a rate $q_3$. Therefore the particles selected through the annular slot 28 are extracted from said slot with a flow rate $q_3-q_2$. Moreover, the following relation is also obtained: $Q=q_0+q_1-q_3+q_2$.

This device makes it possible to deposit the aerosol on the surface of the collection disk 46 under the effect of the electric field $E_2$. In the absence of said electric field, the surface 46 is scavenged by filtered air at rate $q_2$, which guarantees its perfect cleanness, which is not the case in the embodiment described in conjunction with FIG. 5.

The embodiment which has just been described can also be completed by associating, in the manner illustrated in FIG. 7, the collection surface 46 with a detector 54, e.g. a nuclear detector for the analysis of radioactive aerosols. This detector can be identical or similar to the detector 44 described in conjunction with FIG. 6. Moreover, this variant of the apparatus makes it possible to obtain a grain size spectrometer by associating it, as in the case of FIG. 6, with means for processing the signal from the detector 54. Thus, these processing means make it possible to perform a deconvolution or unfolding program so that account can be taken of the two above-described effects, namely:

the time variation, imposed by the user, of the electrical mobility of the particles selected through the slot 28, the decrease, with time, of the activity of the collected radionuclides.

Another embodiment of a spectrometer according to the invention will now be described in connection with FIGS. 8 and 9.

Figure 8:
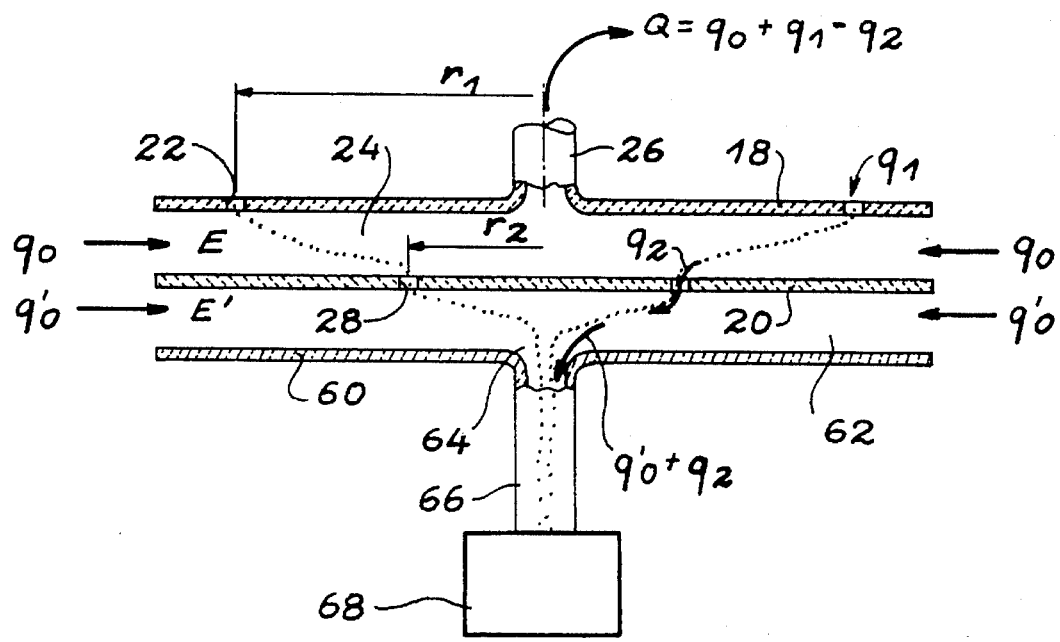
FIGS. 8 & 9 Another two-stage spectrometer according to the invention.

As in the case of the preceding drawings, the spectrometer according to the embodiment of FIG. 8 has a first selection stage for the particles, as a function of their electrical mobility, having the same structure as the selection stage described in conjunction with FIGS. 2A, 2B or 3A and in particular having two concentric, conductive disks 18, 20, each having an annular slot 22, 28. The selection of the particles as a function of their electrical mobility takes place in the manner described hereinbefore.

In addition, the apparatus according to this embodiment has a second stage constituted on the one hand by the second disk 20 described hereinbefore and on the other by a third conductive disk 60 positioned facing the second disk and defining with the latter a space 62. As from the periphery of said space, it is possible to impose with the aid of known means, a radial, filtered air flow rate $q'_0$, which is chosen in such a way that the air flow in the second stage is laminar. Thus, the particles selected through the opening 28 or orifice 29 are channelled as from their extraction from the first stage.

In FIG. 8, an electric field E', obtained by raising each of the disks 20 and 60 to the necessary potential (potential difference V'), can be applied between these two disks so as to "detach" the particles from the surfaces with which they could be in contact. The field E' can be in a simple relationship with the field E:E'=f(E), e.g. E'=E/10. It is in particular possible to impose a dependency of E' on E. This arrangement is not useful in the case of a central extraction (FIG. 9).

The third disk 60 is provided in its center with an opening 64 issuing onto a pipe 66. The center of the opening 64 is preferably aligned with the centers of the disks 18 and 20. The selected particles in laminar flow are confined in the vicinity of the center of the flow, in the axis of the opening 64 and therefore without contact with the walls, i.e. loss-free. Moreover, the trajectories followed by the particles are identical throughout the apparatus, including in the second stage and in the pipe 66, so that the particles flow with identical transit times, which can be easily determined because the geometrical dimensions of the system can also be easily determined.

In both cases (annular slot reduced or not to a central orifice), the particles can then be counted by a detector 68 chosen from among the known systems usually based on optical or electrical methods. In addition, the distance d of the connecting pipe 66 separating the analyzer from the detector 68 can be reduced to the minimum, which offers the advantage of an excellent coupling and which makes it possible to envisage an integration of the analyzer and the detector within the same very compact assembly.

Figure 9:
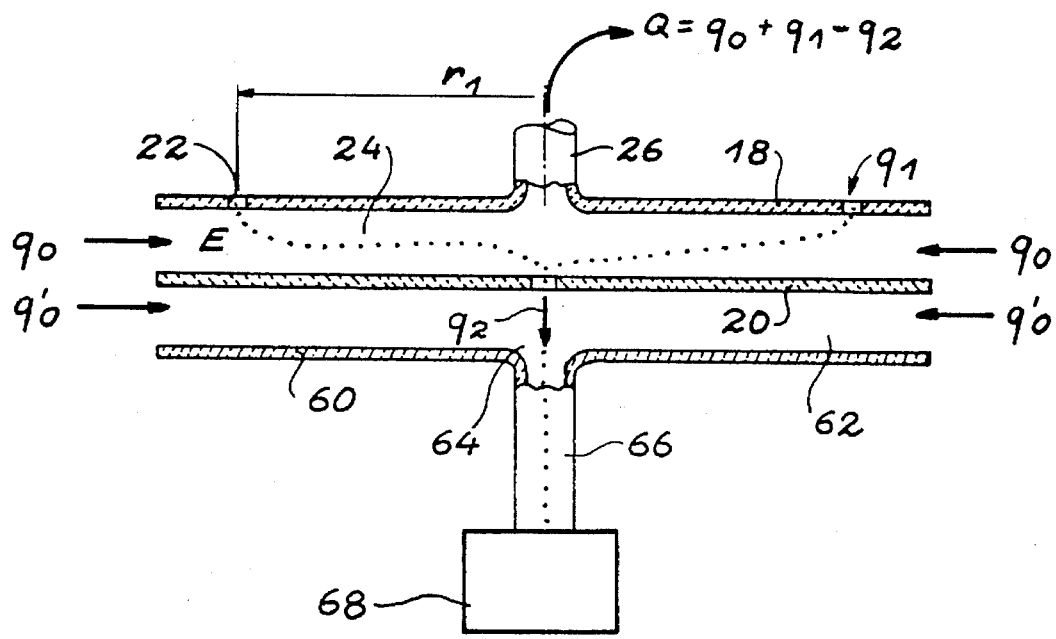
Figure 10:
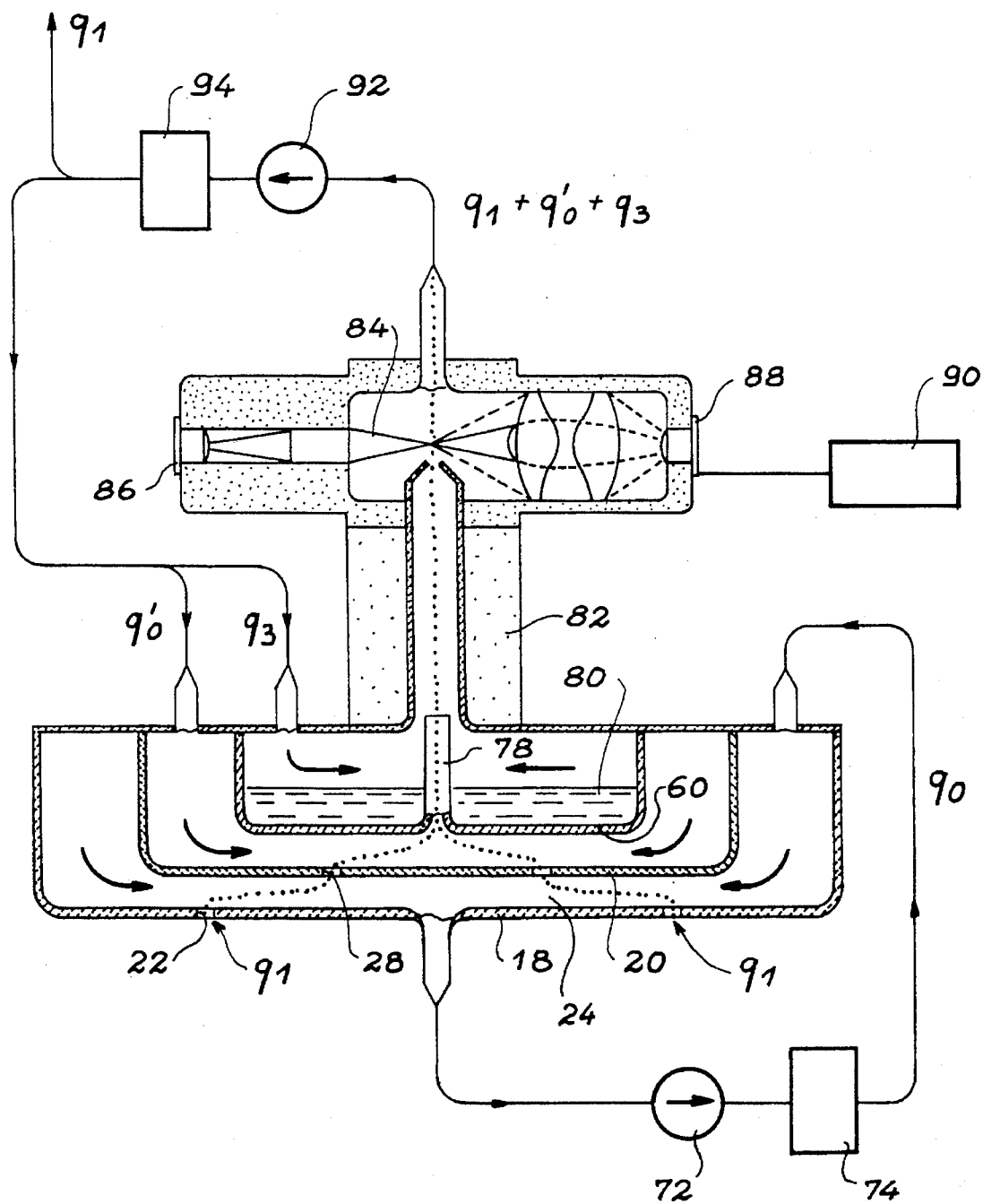
FIGS. 10, 11, 12 In each case a two-stage spectrometer respectively having an optical particle counter, an electrometer and an electron avalanche counter.

A spectrometer according to the latter embodiment using an optical counter as the detector is illustrated in FIG. 10. Thus, unlike in the diagram of FIGS. 8 or 9, the spectrometer is located in the lower part and the optical counter in the upper part, but the operating principle is precisely the same. In FIG. 10 identical references to those used in FIGS. 8 and 9 designate the same components.

From the aeraulic standpoint, the spectrometer is supplied on the one hand with a gas containing the particles to be analyzed (flow rate $q_1$) and on the other with a filtered vector gas (flow rate $q_0$). References 72 and 74 respectively designate a pump and a filter. Means not shown in FIG. 10 are provided for raising the disks 18, 20 and 60 to the desired potentials. During the electrostatic selection, the particles having an adequate mobility are injected into the second stage, then they are entrained by a laminar filtered gas flow (flow rate $q'_0$) and are then transported into the axis of a pipe 78, still in a laminar flow, so as to prevent any contact between the particles and the walls. This small pipe issues at the outlet of a saturator 80, which contains a condensable liquid, whose function is to produce a condensable vapour during the passage of the filtered air flow $q_3$. This makes it possible to enlarge in a condenser 82 the said particles prior to their detection.

The particles are then counted by an optical system using light scattering. The particles to be analyzed are entrained by the gaseous flow through a light beam 84 produced by a source 86. Each particle then scatters a certain light quantity, which is then analyzed by a photodetector 88. Analysis means 90 are provided for collecting data and processing the same.

By introducing the particles into the axis of the saturator, where the saturation is highest, an extremely low particle detection threshold of approximately 1 nanometer is obtained.

This feature, combined with the uniform transit time for the selected particles and the absence of losses by deposition on walls means that the apparatus according to the invention is an extremely precise and sensitive instrument, whilst still being relatively simple and compact.

After traversing the detector, the air is then sucked up to an assembly constituted by a pump 92 and a filter 94 and is then recycled on the one hand to the second stage of the spectrometer (flow rate $q'_0$) and on the other to the saturator 80 (flow rate $q_3$).

Figure 11:
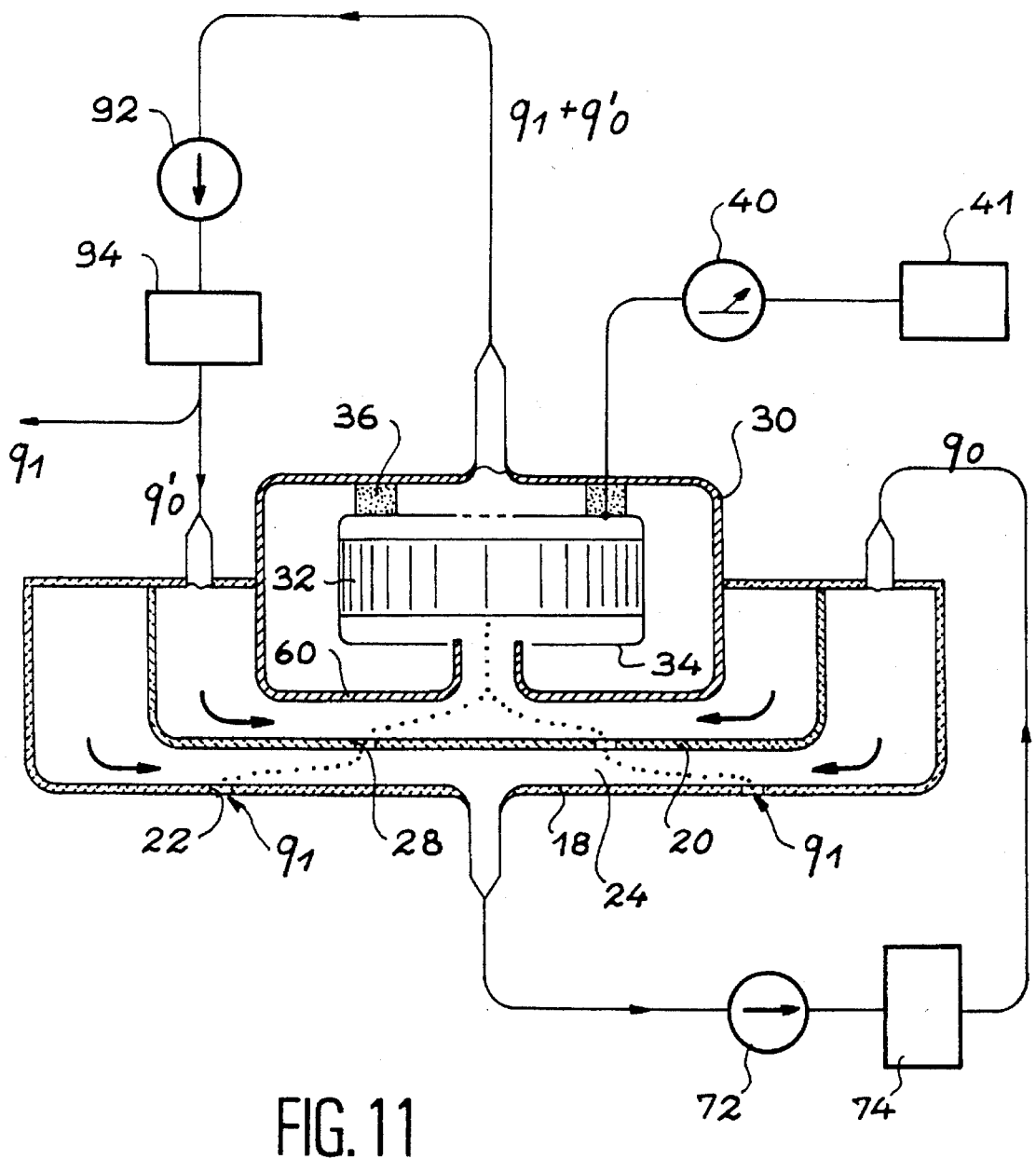

The spectrometer according to the last-mentioned embodiment of the invention (FIGS. 8 and 9) can also function with an electrometer as the detector. This case is shown in FIG. 11, where identical references designate the same components as in FIGS. 8, 9 and 10. The particles are injected by the annular slot 22 and entrained, as hereinbefore, through the two stages. The detector is essentially constituted by identical components to those described in conjunction with FIG. 4, so that these components carry the same references as in FIG. 4.

If N is the concentration of particles to be analyzed, p the average charge carried by each particle, q the sampling flow rate through the filter, the charged particles trapped on the filter 32 induce an electrical current i such that:

$$i = qNpe$$

in which e is the elementary electronic charge.

Here again, the main applications of this method are in the case where |p|=1 (a single electrical charge carried by the particles) and in this case the concentration of particles is directly expressed by:

$$N = i/qe.$$

The detection sensitivity is given by the limits of the hitherto existing electrometers, i.e. approximately $10^{-16}$ amperes. In terms of the concentration of particles N, knowing that N=i/qe, the detection limit for particles carrying a charge is consequently:

for q=1 liter per minute: N=40 particles per $cm^3$, for q=10 liters per minute: N=4 particles per $cm^3$, etc.

One way of improving the detection sensitivity is to increase the sampling flow rate of the particles to be analyzed. This type of detection is also very suitable for the analysis of particles with high concentrations. Finally, the larger the dimensions, the more sensitive is the spectrometer combined with this detector.

For very low concentrations and/or very low flow rates, the aforementioned apparatus is much more suitable than that described hereinbefore.

Figure 12:
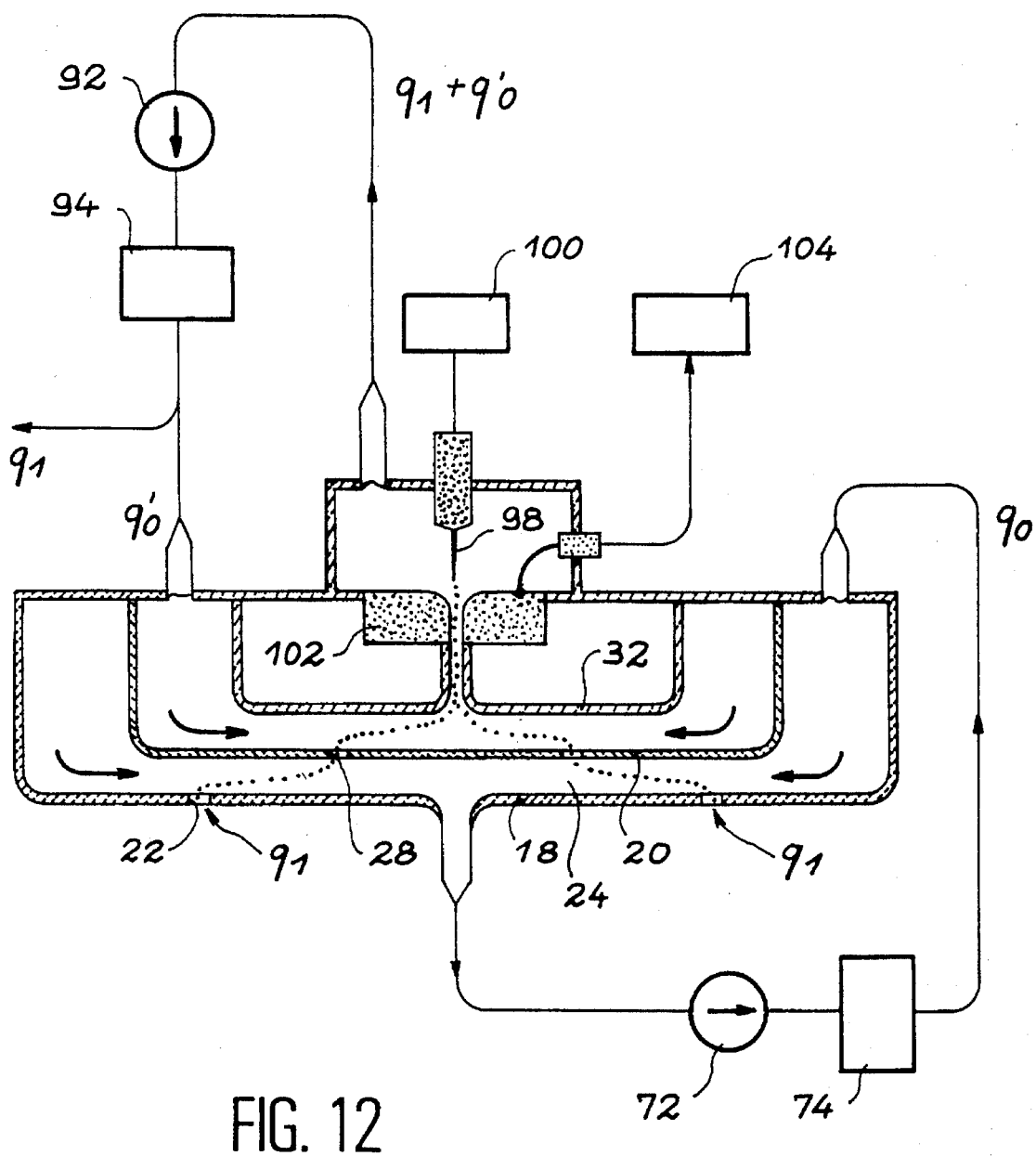

FIG. 12 gives a basic diagram very similar to that given hereinbefore, the difference essentially relating to the use of the electron avalanche detection system. In FIG. 12 identical references designate the same components as in FIG. 11. The detection system essentially has a needle 98 raised to a high positive voltage by a high voltage supply system 100. The value of the high voltage is chosen so as to be just below the initiating voltage of the discharge by "corona effect", as in a Geiger counter. When a negative particle comes into the vicinity of the electrode, in a region where the electric field is very intense, an electron is detached from the particle and immediately causes an electronic avalanche, which induces a current pulse which can easily be detected by a collector 102 connected to a pulse counter 104.

One of the advantages of the latter apparatus type is that it lends itself to extensive miniaturization, the size of a sensor of the type described can be as small as a few centimetres in diameter.

The embodiments given in conjunction with FIGS. 10 to 12 can also be used with a spectrometer, whose annular opening 28 is reduced to a central orifice, as described hereinbefore in conjunction with FIG. 9.

For all the apparatuses described hereinbefore (FIGS. 10 to 12), one method for determining the grain size distribution of submicron aerosols consists of establishing the mobility spectrum of the particles by performing a rapid mobility scan of the particles with the aid of the means provided for this purpose, e.g. a scan of the field E=f(t). Then, on the basis of the knowledge of the following data:

charge law of the initial particles as a function of their size, value of the different flow rates, dimensional characteristics of the apparatus, functions E=f(t), E'=g(t), particle transit time in the different compartments, counting rate of the pulses as a function of time, it is possible to automatically return to the grain size spectrum of the initial particles by means of a computing program functioning on a microcomputer specially designed for this purpose. Such a program is based on a computing method like that described in the article by S. C. Wang et al, entitled "Scanning electrical mobility spectrometer", published in Aerosol Science and Technology, vol. 13, pp 230–240, 1990.

A spectrometer having to cover a wide concentration range can combine two detector types, namely an electronic avalanche counter and an electrometer. In such an apparatus, the detectors are connected in series in the same assembly and used in their respective concentration range. There is a very considerable analogy with the principle of certain optical detectors of the condensation type, which can operate either in the pulse mode for low concentrations, or in the integrated mode for higher concentrations.

I claim:

1. Electrical mobility spectrometer for aerosol particles contained in an atmosphere to be examined, comprising a first and a second, spaced, parallel, coaxial conductive disks between which is established an electric field by raising said first and second coaxial conductive disks to different potentials, the space between the first and second conductive disks communicating with the atmosphere to be examined through an annular slot having a first radius made in the first coaxial conductive disk, a central intake being provided in order to bring about circulation in said space, from the periphery of the disks, of a stable centripetal, laminar filtered air flow, and the second coaxial conductive disk is provided with an opening so as to permit the selection of aerosol particles having a given electrical mobility, and further comprising means able to vary the selected electrical mobility and an aerosol detector, the aerosol detector being placed immediately under the opening of the second disk.

2. Spectrometer according to claim 1, the opening in the second disk being an annular opening having a second radius, wherein said first radius is greater than said second radius.

3. Spectrometer according to claim 1, the opening in the second disk being a single central extraction orifice.

4. Spectrometer according to one of the claims 1 to 3, the aerosol detector being an electrometer.

5. Spectrometer according to one of the claims 1 to 3, the aerosol detector being a nuclear detector.

6. Submicron aerosol grain size spectrometer comprising the electrical mobility spectrometer according to one of the claims 1 to 3 and means for processing the signal obtained by the detector programmable in such a way as to obtain, from the electrical mobility spectrum obtained at the detector outlet, a grain size spectrum of the aerosol.

7. Electrical mobility spectrometer for aerosol particles contained in an atmosphere to be examined, comprising a first and a second, spaced, parallel, coaxial conductive disks between which is established an electric field by raising said first and second coaxial conductive disks to different potentials, the space between the first and second conductive disks communicating with the atmosphere to be examined through an annular slot having a first radius made in the first coaxial conductive disk, a central intake being provided in order to bring about the circulation in said space, from the periphery of the first and second coaxial conductive disks, of a stable, centripetal, laminar filtered air flow, and the second coaxial conductive disk is provided with an opening so as to permit the selection of aerosol particles having a given electrical mobility, and further comprising means able to vary the selected electrical mobility and an aerosol collector, the aerosol collector being placed immediately under the opening the second disk.

8. Electrical mobility spectrometer according to claim 7, the opening in the second disk being an annular opening having a second radius, wherein said first radius is greater than said second radius.

9. Electrical mobility spectrometer according to claim 7, the opening in the second disk being a single central extraction orifice.

10. Spectrometer according to one of the claims 7 to 9, the collector being of the electrostatic type.

11. Spectrometer according to claim 10, the collector being provided with a nuclear detector for the analysis of radioactive aerosols.

12. Spectrometer according to one of the claims 7 to 9, the collector comprising:

a third conductive disk facing the second coaxial conductive disk to form a space therebetween and forming a collection surface for the selected particles, means for injecting into the space between the second and third disks a radial, laminar, filtered air flow from the periphery of said second and third disks, and a central pipe fixed to the second disk permitting the suction of the atmosphere between the second and third disks.

13. Spectrometer according to claim 12, the collector also being provided with a nuclear detector for radioactive aerosol analysis.

14. Electrical mobility spectrometer, according to one of claims 7 to 9, said aerosol collector being connected to a detector.

15. Submicron aerosol grain size spectrometer comprising said electrical mobility spectrometer according to claim 14 and means for processing the signal obtained by the detector programmable in such a way as to obtain, from the electrical mobility spectrum obtained at the detector outlet, a grain size spectrum of the aerosol.

16. Spectrometer according to one of the claims 7 to 9, the collector being a mechanical collector.

17. Spectrometer according to claim 16, the mechanical collector being connected to an electrometer.

* * * * *